United States Patent [19]

Seibert

[11] 4,052,817
[45] Oct. 11, 1977

[54] PROCESS FOR STORING AND RECOVERING PLANT TISSUE

[75] Inventor: Michael Seibert, Lynnfield, Mass.

[73] Assignee: GTE Laboratories Incorporated, Waltham, Mass.

[21] Appl. No.: 731,146

[22] Filed: Oct. 12, 1976

Related U.S. Application Data

[63] Continuation-in-part of Ser. No. 660,289, Feb. 23, 1976, abandoned.

[51] Int. Cl.$^2$ .............................................. A01G 1/00
[52] U.S. Cl. ........................................................ 47/58
[58] Field of Search ............................................ 47/58

[56] References Cited

PUBLICATIONS

Cultivation of Animal & Plant Cells, White, 2nd Ed., 1963, Ronald Press Co., N.Y., p. 180 cited.

3rd Ann. Cong. of Plant Tissue & Cell Culture, Leicester, Eng., 1974, Paper No. 95 relied on, papers 94, 96.

Primary Examiner—Robert E. Bagwill
Attorney, Agent, or Firm—Irving M. Kriegsman

[57] ABSTRACT

Meristematic tissue such as from shoot apices of herbaceous plants in a freezing solution containing a cryoprotectant are cooled to a temperature of at least $-70°$ C, stored when frozen and subsequently thawed at an average warming rate of at least about 24° C/min when the tissue is at a temperature between about $-70°$ C and about $-10°$ C to obtain pathogen-free meristematic tissue having morphogenic potential. The donor plants from which the tissue is to be excised are cold treated to induce cellular reactions believed to be related to the winter cold hardening process, generally at a temperature between the plant freezing temperature and about 10° C.

5 Claims, No Drawings

PROCESS FOR STORING AND RECOVERING PLANT TISSUE

This application is a continuation-in-part of application Ser. No. 660,289, filed Feb. 23, 1976 and now abandoned.

BACKGROUND OF THE INVENTION

This invention relates to a process for storing by freezing and subsequently recovering meristematic plant tissue as from the shoot apex having chlorophyll synthesis ability and morphogenic potential.

Unorganized callus tissues derived from plants have been propogated and differentiated into plants under the influence of growth hormones, however, such tissues exhibit genetic instability, chromosomal abnormalities, and often lose the ability to initiate organs after numerous subculturing steps. Since a plant obtained from such a culture is not necessarily identical to the parent, such a technique cannot be used as a propogation or storage method where identical plants are needed or desired. In addition, development, if it can take place in callus and cell cultures derived from callus or other plant tissue, also involved adventitious organogensis of either shoots or asexual embryos which can foster a high incidence of genetically aberrant plants.

Procedures for propogating and thus storaging plants involving serial transfer or subculturing of meristematic tissue as in adventitious or auxiliary shoot multiplication wherein the cultures are grown on a suitable growth medium are disadvantageous since eventual chromosomal changes occur so that the desirable characteristics of the parent plant cannot be obtained. Also, subcultures are lost through equipment failures. In addition, the tissue explants are subject to accidental contamination by microorganisms after extended subculturing.

Plants also are presently propogated from meristematic tissue by excising it from a donor plant and placing it in a growth medium. In some cases, as with pineapple or strawberry meristematic tissue, the explant is placed in a medium or under low above freezing temperatures (minimal growth conditions) which promotes only slow growth. The process requires that liquid medium be added to this tissue every few months to prevent dessication, thus exposing the cultures to microorganism contamination. In addition, using present processes, meristematic tissue cannot be stored indefinitely without its growing to a degree where the growth must be continued to maturity to sustain the plant. Therefore, the effective storage time for such tissue is greatly and undesirably limited.

Prior to the present invention, plant material has been frozen for storage and subsequently thawed while maintaining cell viability. Plant material processed in this manner includes cell culture cells, asexual embryos obtained from cell cultures and callus. While cell cultures are amenable to breeding by the fusion of haploid or diploid cells from different plants, in most species great difficulty is encountered in obtaining differentiation to a whole plant. Also, cell cultures can foster the same high incidence of genetically aberrant plants as do callus cultures. In addition, asexual embryos are not formed in a wide variety of plant species. Finally, the induction, maintenance and freezing of cell or embryo cultures at low freezing rates and recovery, thereof, requires a great deal of specialized skill and equipment.

Accordingly, present processes for storing plant cultures are deficient in that there are no reliable methods which permit initiation of growth of daughter plants in a wide variety of plant species for long periods after initial derivation of tissue from the parent plant and for assuring exact genetic duplication of parent plants which are essentially pathogen-free.

SUMMARY OF THE INVENTION

In accordance with this invention, donor plants which are the source of meristematic tissue such as is derived from the shoot apex or shoot tip from herbaceous plants first are cold treated at a temperature and for a time which induces cellular processes believed to be related to the winter cold hardening process to avoid lethal intracellular ice crystallization. The meristematic tissue then is excised from the donor plant and is cooled in a freezing solution at a high cooling rate to a temperature below about $-70°$ C to stop essentially all cellular processes and immobilize enzymatic activity in the tissue. When it is desired to propogate a plant from the frozen meristematic tissue, the tissue and freezing solution are warmed at a relatively high rate and exposed to environmental conditions such as light intensity and length, temperature, humidity and growth medium composition optimum for growth. After the meristematic tissue has developed, it can be planted in soil to effect growth to a mature plant.

DESCRIPTION OF SPECIFIC EMBODIMENTS

The present invention provides a process for growing essentially pathogen-free plants which are exact genetic duplicates of a parent plant wherein plant growth can be initiated over long periods after deriving plant tissue from a parent plant. In addition, the present process provides a high survival rate and high differentiation rate of the treated tissue. This process provides substantial advantages over the prior art since it permits the use of the specific plant parts from which essentially internal pathogen-free duplicate plants can be reliably obtained in a wide variety of plant species without the risk of accidental microorganism contamination, equipment failure or changes in chromosomal cytology and morphogenic potential.

In accordance with this invention, donor plants or organ tissue cultures from which meristematic tissue is to be excised are cold treated to induce cellular reactions possibly related to the winter cold hardening process to avoid lethal intracellular ice crystallization. Cold treatment is effected at a temperature between that at which the plants freeze and $10°$ C, preferably between about $3°$ C and $5°$ C for a time of at least about 1 day and usually between 3 days and 70 days. In this manner, the desired cellular reaction believed to be related to the winter cold hardening process is achieved without damage to the tissue cells. The meristematic tissue, in particular the shoot apical dome and which also may include leaf primordia, but also including such other meristematic tissue, such as obtained from root tips, buds, ovules and cambium tissue, is excised from a plant. Only the herbaceous species which can be grown from shoot apices can be processed in accordance with this invention. Representative suitable plants include *Dracaena sp., Yucca sp., Philodendron sp., Chrysantheum morifolium, Gerbera jamesonii, Begonia sp., Dianthus caryophyllus, Pelargonium hortorum, Asparagus officinalis, Gloxinia sp., Gladiolus hortulans, Malus sp., Lilium longiflorum, Lactuca sativa, Saccharum sp., Musa cavendishii, Saxifrage sp., Nicotiana rustica L.* and the like. Particularly good results have been obtained by processing *Asparagus officinalis*, *Lactuca sativa* and *Caryophyllaceae* specifically *Dianthus caryophyllus*.

The meristematic tissue then is placed in a freezing solution containing a cryoprotectant in growing medium consisting of inorganic salts, organics and plant hormones. The growing medium will promote growth of the meristematic tissue when it is thawed. The medium is selected in accordance with the species being treated as is well known to obtain optimum growth. Representative suitable cryoprotectants include dimethyl sulfoxide (DMSO), glycerol, sucrose, polyvinylpyrrolidone, mixtures thereof or the like in the usual concentrations for the cryoprotectant. Representative concentrations for DMSO are between about 1 and 35% (v/v), usually between 2.5 and 10% (v/v) of the total freezing medium. The meristematic tissue is incubated in the freezing solution containing a cryoprotectant such as DMSO prior to freezing in order to cause diffusion of the cryoprotectant into the tissue.

The freezing solution and tissue in a suitable container such as a glass vial then are frozen to a temperature below at least about $-70°$ C, in order that tissue growth be suspended without substantially adversely affecting the morphogenic potential of the tissue. Cooling rates as measured between $-10°$ C to $-70°$ C can be as low as about 1° C/min with the cooling rates equal to or greater than 50° C/min being preferred. The tissue and growth medium can be maintained frozen at these low temperatures for periods of at least about 5 min up to an indefinite period until thawing is desired so that the morphogenic potential of the tissue is not substantially destroyed. Freezing can be effected by any conventional means such as by pouring liquid nitrogen into the vial and maintaining the vial in liquid nitrogen or by using any available freezing rate controller device.

When it is desired to develop the tissue into a plant, it and the freezing solution are thawed to a suitable growing temperature at an average warming rate of at least about 24° C/min when the tissue is at a temperature between about $-70°$ C and about $-10°$ C, preferably at above 100° C/min. It has been found that when thawing is effected at a rate of less than about 24° C/min, viable growth is small. Thawing can be effected by any conventional means including placing a vial containing the frozen tissue and freezing medium into water at 37° C or by using any warming rate controlling device.

The thawed tissue is exposed to environmental conditions suitable for optimum plant growth wherein light intensity, duration and type as well as conditions of temperature and relative humidity are regulated. After growth has been obtained in the growth medium, the tissue can be transplanted to soil for growth to a mature plant.

The following examples illustrate the present invention and are not intended to limit the same.

EXAMPLE I

This example illustrates that a shoot apex of carnations can be cold treated, frozen and thereafter successfully thawed to a viable state.

*Dianthus caryophyllus* cultivars 'Scania' and 'Linda' were obtained as rooted cutting from commercial sources. The cuttings were planted in a commercial potting mix containing vermiculite, perlite and peat at high density (150 cuttings in a 2000 cm² flat). Cold treatment was accomplished by placing flats of cuttings in an environment chamber (Controlled Environments, Ltd., Winnipeg, Canada) under the following conditions: temperature, 4° C; photoperiod, 8 hours per day; light irradiance, cool white fluorescent — 0.5 mW/cm² between 400–700 nm (1500 lux)-plus incandescent — 0.036 mW/cm² between 400–700 (80 lux).

Carnation shoot apices, including the meristem and 2 sets of leaf primordia (unless otherwise stated), were excised from surface sterilized shoot tips which had been peeled back to 4 or 5 sets of leaves. In order to be classified as a usable shoot apex, the ends of the 2nd set of leaf primordia had to at least cover the meristem dome and touch. Such apices were 1 to 2.5 mm long depending on the size of the older pair of leaf primordia.

Sample apices were floated in 5 ml specimen vials on 0.25 ml of a rinsing solution (M. Seibert, *Science*, 191: 1178–79, 1976) containing Murashige and Skoog salts (1962 *Physiol. Plant* 15: 473), 30 g/l sucrose, 0.4 mg/l thiamine HCl, 100 mg/l myoinositol, 0.1 mg/l indoescetic acid and 0.5 mg/l kinetin with the pH adjusted to 5.7. At the desired time, an additional 0.25 ml of rinsing solution at twice the final desired dimethyl sulfoxide (DMSO) concentration was added to the vial to make up the freezing solution. For DMSO concentrations greater than 10%, the shoot apices were added to the freezing solution at time zero.

Samples were cooled by pouring liquid nitrogen directly into the freezing vial while dipping the vial directly into an open Dewar flask filled with liquid nitrogen. This gave an average cooling rate of 400° to 440° C/min and a maximum cooling rate of 850° to 1100° C/min between $-10°$ and $-70°$ C. Microorganism contamination was not a problem. Other cooling rates (between $-10°$ and $-70°$ C) were obtained by suspending experimental freezing vials over liquid nitrogen and manually adjusting the distance of the vials from the nitrogen. The desired rate was maintained by comparing the output slope from a copper:constantan thermocouple located at the liquid surface in a dummy freezing vial with a pre-calculated slope on a pen recorder chart. After the temperature reached $-80°$ C the vials were plunged directly into liquid nitrogen. All samples were kept in liquid nitrogen for at least 30 minutes.

Shoot apices were thawed by plunging the vials into 37° C water. Such conditions gave an average initial warming rate of around 1450° C/min. This is roughly equivalent to an average warming rate of about 180° C/min when the tissue is at a temperature between about $-70°$ C and about $-10°$ C. The slower initial warming rates were obtained by warming the vials in air or blowing air past the vials.

After warming to room temperature, the thawed apices were washed twice in rinsing solution and then planted in 25 × 125 mm Belco tubes on a growing medium consisting of the rinsing solution solidified with 1% bacto-agar (DIFCO). The tubes were placed in growing cabinets at 26 ± 2° C with 16 hour/day exposure to light from Gro-Lux fluorescent lamps (0.43mW/cm² from 400–700 nm or 600 lux). Shoot apices which formed chlorophyll or which showed signs of growth or differentiation were termed surviving apices. Differentiating apices were defined as those which formed new leaf primordia or shoots.

In order to determine whether or not cold treatment of donor plants affects the rate of survival of excised, frozen shoot apices, a number of plants were exposed to 4° C in an incubator for about seven weeks. Two weeks after subjecting 40 shoot apices to a freeze/thaw cycle, all 40 apices showed signs of survival and 24 (60%) appeared to be differentiating. This constituted a large improvement over the 30% survival rate and less than 5% differentiation rate for frozen shoot apices obtained from plants which were not cold treated, (M. Seibert, 1976 *Science,* 191:1178-79). Even with shorter periods of cold treatment, improvements in plant survival were obtained. Three days exposure to 4° C was sufficient to elicit more than a doubling in the percentage of frozen shoot apices which survived freezing and a 6 to 7-fold increase in the percentage which formed leaf primordia or shoots.

Since the size of the explant might influence survival and differentiation, shoot apices with from 1 to 4 sets of leaf primordia were excised from cold treated plants. The ends of the largest leaves were removed in the case of apices containing 4 sets of leaf primordia so that the apices would fit into the freezing vial. Table I shows the effect on survival 1 week after thawing and on differentiation 1 month after thawing. The data reported in Table I were obtained under the following conditions. Donor plants were exposed to 4° C for 14 days. After cold treatment, shoot apices were excised from the cuttings, treated with 5% DMSO for 85 minutes, frozen to −196° C by pouring liquid nitrogen directly into the freezing vial, thawed by placing the vial in 37° C water, washed twice in rinsing solution and planted in growing medium. Maximal survival rates occured in apices containing 2 or 3 sets of leaf primordia and maximal differentiation rates in apices containing 2 sets of leaf primordia or more. Although the rate of differentiation for treatment 4 was statistically indistinguishable from those of treatments 2 or 3, much more callus formation was noted.

The presence of a cryoprotectant, such as DMSO in this case, in addition to cold treatment is desirable in order to obtain high rates of survival and differentiation after subjecting carnation shoot apices to a freeze/thaw cycle. The results show that treatment with 5% DMSO for 80 to 100 minutes appears optimal for both survival and differentiation.

Maximal survival and differentiation occur at cooling rates above about 50° C/min. Maximal survival and differentiation rates occur at the fastest average warming rate tested which was about 180° C/min when the tissue was at a temperature between about −70° C and about −10° C.

TABLE I

Effect of Shoot Apex Size on Survival and Differentiation After a Freeze/Thaw Cycle

| Treatment | Number of Sets of Leaf Primordia | Number of Apices Frozen | Survival 1 Week After Thawing (%) | Differentiation 1 Month After Thawing (%) |
|---|---|---|---|---|
| 1 | 1 | 24 | 67 | 17 |
| 2 | 2 | 34 | 91 | 47 |
| 3 | 3 | 26 | 92 | 58 |
| 4 | 4 | 29 | 72 | 48 |

EXAMPLE II

This example illustrates that a shoot apex of asparagus can be cold treated, frozen and thereafter successfully thawed to a viable size.

Plants of asparagus, *Asparagus officinalis,* were maintained over a period of about 4 years by subculturing shoot apices. Donor cultures were exposed to 4° C for the number of days indicated in Table II. Shoot apices were excised from cultured tissue which was in a growing medium of Murashige et al (1972 *J. Amer. Soc. Hort. Sci.* 97: 158-161). The pH of the growing medium was adjusted to 5.7 by adding NaOH before addition of 6 g/l agar. The apices were placed in a 4 ml glass vial containing 0.5 ml of a freezing solution consisting of 5% (v/v) DMSO in the growing medium (minus agar) for about 85 minutes. The shoot apices were 0.5 to 2 mm in diameter at this stage. Freezing was accomplished by pouring liquid nitrogen directly into the freezing vial and then dipping the vial into an open dewar filled with liquid nitrogen. The cooling rate (between −10° C and −70° C) was measured using a copper:constantan thermocouple at the liquid surface (most of the apices floated) and was ≧ 400° C/min. The apices were frozen for a period of 30 minutes. Shoot apices were thawed by plunging the vials into 37° C water to give an average warming rate of about 180° C/min (between −70° C and −10° C). Thawed apices were rinsed twice in liquid growing medium (minus DMSO) and then transferred to tubes containing the agar growing medium.

Survival was shown to have occurred by virtue of growth or chlorophyll formation in the thawed samples. Differentiation was demonstrated by spear formation.

TABLE II

Survival of Cold Treated Asparagus Organ Cultures After a Freeze/Thaw Cycle

| Treatment | Number of Frozen Apices | % Survival | % Differentiation |
|---|---|---|---|
| Experiment 1[1] Control (No Cold Treat) | 30 | 30 | 13 |
| Experiment 2[1] Control (No Cold Treat) | 35 | 28 | 6 |
| Cold Treatment[1] for 33 Days | 21 | 57 | 38 |

[1]Data obtained 3 months after thawing

EXAMPLES III

This example illustrates that a shoot apex of lettuce can be cold treated, frozen and thereafter successfully thawed to a viable state.

Shoot apices having 2 sets of leaf primordia were excised from the one month old lettuce plants, *Lactuca sativa,* which were exposed to 4° C for the number of days indicated in Table III and were placed in a rinsing solution including Murashige and Skoog salts (1962 *Physiol. Plant.* 15: 473) organics and plant hormones. The pH of the rinsing solution was adjusted to 5.7 by adding NaOH. Addition of 10 g/l agar constituted the growing medium. The apices were placed in a 4 ml glass vial containing 0.5 ml of a freezing solution consisting of 5% (v/v) DMSO in the rinsing solution for 85 minutes. The shoot apices were about 0.5 to 2 mm long at this stage. Freezing was accomplished by pouring liquid nitrogen directly into the freezing vial and then dipping the vial into an open dewar filled with liquid nitrogen. The cooling rate (between −10° C and −70° C) was measured with a copper:constantan thermocouple at the liquid surface (most of the apices floated) and was ≧ 400° C/min. The apices were frozen for a period of 30 minutes. Shoot apices were thawed by plunging the vials into 37° C water to give an average warming rate of about 180° C/min (between −70° C and −10° C). Thawed apices were rinsed twice in rinsing solution and then transferred to tubes containing the agar growing medium.

Survival was shown to have occurred by virtue of chlorophyll formation and growth in the thawed apices. Differentiation was demonstrated by shoot formation.

TABLE III

Survival of Cold Treated Lettuce Shoot Apices After a Freeze/Thaw Cycle

| Treatment | Number of Frozen Apices | % Survival | % Differentiation |
| --- | --- | --- | --- |
| Greenhouse Grown (No Cold Treat) | 23 | 0 | 0 |
| Greenhouse Grown + Cold Treatment for 37 Days | 18 | 56 | — |
| Greenhouse Grown + Cold Treatment for 58 Days | 21 | 67 | 52 |

I claim:

1. A process for providing herbaceous plants which comprises cold treating a donor herbaceous plant without damaging the meristematic tissue of the plant, excising the meristematic tissue of the donor plant, placing the tissue in a composition comprising a rinsing solution and a cryoprotectant, rapidly freezing the tissue and composition to a temperature below about $-70°$ C, thawing the tissue and composition at an average warming rate of at least about $24°$ C/min when the tissue is at a temperature between about $-70°$ C and about $-10°$ C and exposing the thawed tissue to an environment of temperature, light, humidity and growth medium which promotes growth of the tissue to a mature plant.

2. The process of claim 1 wherein the plant is a *Dianthus*.

3. The process of claim 1 wherein the plant is *Dianthus caryophyllus*.

4. The process of claim 1 wherein the plant is *Asparagus officinalis*.

5. The process of claim 1 wherein the plant is *Lactuca sativa*.